US008566119B2

(12) United States Patent  (10) Patent No.: US 8,566,119 B2
Lei  (45) Date of Patent: *Oct. 22, 2013

(54) METHOD OF PICTURE ARCHIVING COMMUNICATION SYSTEM MESSAGING INTELLIGENT UPDATE MECHANISM

(75) Inventor: Weng I. Lei, Mount Prospect, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1224 days.

This patent is subject to a terminal disclaimer.

(21) Appl. No.: 11/837,805

(22) Filed: Aug. 13, 2007

(65) Prior Publication Data

US 2008/0275735 A1   Nov. 6, 2008

Related U.S. Application Data

(60) Provisional application No. 60/916,021, filed on May 4, 2007.

(51) Int. Cl.
    *G06Q 10/00* (2012.01)
    *G06Q 50/00* (2012.01)
    *G06Q 40/00* (2012.01)

(52) U.S. Cl.
    USPC ........................................ 705/3; 705/2; 705/4

(58) Field of Classification Search
    USPC .......................................................... 705/2–3
    See application file for complete search history.

(56) References Cited

U.S. PATENT DOCUMENTS

| 4,833,625 | A | 5/1989 | Fisher |
| 4,843,471 | A | 6/1989 | Yazawa |
| 5,359,512 | A | 10/1994 | Nishihara |
| 5,823,948 | A * | 10/1998 | Ross et al. ............... 600/300 |
| 5,915,242 | A | 6/1999 | Tsujii |
| 5,926,526 | A * | 7/1999 | Rapaport et al. ........ 379/88.25 |
| 6,127,669 | A | 10/2000 | Sidiropoulos |
| 6,151,404 | A | 11/2000 | Pieper |
| 6,256,613 | B1 * | 7/2001 | Falchuk et al. ............... 705/2 |
| 6,370,413 | B1 | 4/2002 | Alvarez |
| 6,411,836 | B1 | 6/2002 | Patel |
| 6,895,128 | B2 | 5/2005 | Bohnenkamp |
| 6,957,095 | B2 | 10/2005 | Matsui |
| 7,058,901 | B1 | 6/2006 | Hafey |
| 7,076,111 | B2 | 7/2006 | Shinbata |
| 7,076,436 | B1 * | 7/2006 | Ross et al. ............... 705/3 |

(Continued)

OTHER PUBLICATIONS

Kehoe, Bob, "Nurses communicate with wireless badges", Materials Management in Health Care, Jun. 1, 2006.*

Primary Examiner — Jason Dunham
Assistant Examiner — Amber A Misiaszek
(74) Attorney, Agent, or Firm — Peter R. Withstandley

(57) ABSTRACT

A system and method for medical scan archiving and notifying medical professionals of a need for evaluation of the medical scan, having the steps of enrolling a medical professional in a computer system, the enrolling of the medical professional including a medical professional type, gathering medical data from the patient, entering the medical data gathered from the patient, an urgency type for the patient, and a medical data type for the patient into a data archival system, evaluating the urgency type for the patient related to the medical data, conducing a broadcast message to a medical professional with a medical professional type corresponding to the medical data type when the urgency type corresponds to a need for immediate reading of the medical data for the patient and retrieving the broadcast message to the medical professional and conducting a replacement broadcast when the urgency type of the medical data changes from a first state to a second state.

17 Claims, 2 Drawing Sheets

(56) References Cited

U.S. PATENT DOCUMENTS

| | | |
|---|---|---|
| 7,162,623 B2 | 1/2007 | Yngvesson |
| 7,212,661 B2 | 5/2007 | Samara |
| 7,761,308 B2 * | 7/2010 | Falchuk et al. .................. 705/2 |
| 2003/0055679 A1 * | 3/2003 | Soll et al. .......................... 705/2 |
| 2005/0203775 A1 * | 9/2005 | Chesbrough ..................... 705/2 |
| 2006/0277075 A1 * | 12/2006 | Salwan ............................. 705/3 |
| 2007/0041626 A1 * | 2/2007 | Weiss et al. .................. 382/131 |
| 2007/0083403 A1 * | 4/2007 | Baldwin et al. .................. 705/7 |

\* cited by examiner

METHOD OF PICTURE ARCHIVING COMMUNICATION SYSTEM MESSAGING INTELLIGENT UPDATE MECHANISM

CROSS-REFERENCE TO RELATED APPLICATIONS

This is a U.S. non-provisional application of U.S. provisional patent application Ser. No. 60/916,021 filed May 4, 2007 by Weng I Lei the entirety of which application is incorporated by reference herein.

FIELD

The invention relates to a system and method for medical data archiving. More specifically, the invention provides an intelligent message broadcast mechanism for the Picture Archiving And Communication Systems (PACS) to alert medical professional of the need to evaluate the medical data scans and retrieve outdated message broadcasts.

BACKGROUND INFORMATION

Evaluation of medical data by medical professionals is a necessary and important process in medical care. Systems used by medical professionals must have the ability to accurately recall and present data from medical tests to medical evaluative professionals. These systems must also allow for long term storage of the data to allow comparison of differing data sets over time.

In some instances, evaluations are to be performed in a non-emergency time frame as no emergency exists. On other occasions, however, when an emergency condition exists, the data from medical tests must be evaluated quickly. In these emergency situations, if medical professionals are not immediately present, the medical data goes unread and unevaluated, delaying patient care.

Conventional paging systems retain messages to medical professionals that contain data that is old or redundant, causing the medical professional to spend valuable time clearing messages from the messaging system and possibly take action on exams that my have been processed by other radiologists, thereby creating an inefficiency.

There is a need to provide a method and apparatus to notify medical professionals, such as radiologists, that examination of medical data should commence when data is ready.

There is a further need to provide a method and apparatus to minimize time lag between preparation of medical data and evaluation by medical professionals so that patients receive immediate care.

There is a still further need to provide a method and system that will minimize the need for emergency examination readings that are not necessarily needed to be processed on an expedited basis.

There is also a need to provide a method and system that will discriminate between data types and subsequently allow notification of appropriate medical professionals based upon the data type required to be evaluated.

There is a further need to provide a method and system that has an intelligently designed messaging system such that messages that are beyond a certain age or wherein data has changed status during an intervening time interval, are retrieved by the system.

SUMMARY

It is therefore an objective to provide a method and apparatus to notify medical professionals, such as radiologists, that examination of medical data should commence.

It is a further objective to provide a method and apparatus to minimize time lag between preparation of medical data and evaluation by medical professionals so that patients receive immediate care.

It is a still further objective to provide a method and system that will minimize the need for emergency examination readings that are not necessarily needed to be processed on an expedited basis.

It is also an objective to provide a method and system that will discriminate between the data types and subsequently allow notification of appropriate medical professionals based upon the data type required to be evaluated.

There is a further objective of the method and system to provide an intelligently designed messaging system for the picture archiving communication system such that messages that are beyond a certain age or wherein data has changed status during the intervening time interval, are retrieved by the system.

The invention provides a method for medical scan archiving and notifying medical professionals of a need for evaluation of the medical scan, comprising the steps of enrolling a medical professional in a computer system, the enrolling of the medical professional including a medical professional type, gathering medical data from a patient, entering the medical data gathered from the patient, an urgency type for the patient, and a medical data type for the patient into a data archival system, evaluating the urgency type for the patient related to the medical data, conducting a broadcast message to a medical professional with a medical professional type corresponding to the medical data type when the urgency type corresponds to a need for immediate reading of the medical data for the patient, and retrieving the broadcast message to the medical professional and conducting a replacement broadcast when the urgency type of the medical data changes from a first state to a second state.

The method of the invention may also be accomplished such that the urgency type for the patient is at least one of a modality categorization, an exam priority categorization, a study data categorization and a time categorization. The method may, further comprise the step of verifying the urgency type for the patient after the step of evaluating the urgency type for the patient related to the medical data and before the step of conducting the broadcast message to the medical professional. The method may also further comprise the step of reading the medical data by a medical professional. The method may further comprise changing the urgency type in the data archival system after the reading of the medical data by the medical professional. The medical data type may have differing modalities, such as a magnetic resonance image or a computed tomography image, as non-limiting examples.

In addition to the above, the method may further comprise the step of creating a notification list of medical professionals of a same medical professional type; wherein the conducting of the broadcast message to the medical professional with the medical professional type corresponding to the medical data type when the urgency type corresponds to a need for immediate reading of the medical data for the patient is done through contacting medical professionals on the notification list.

In another exemplary embodiment of the invention, a program storage device readable by machine is presented, tangibly embodying a program of instructions executable by the machine to perform method steps for medical scan archiving and notifying medical professionals of a need for evaluation of the medical scan, comprising the steps of enrolling a medical professional in a computer system, the enrolling of the medical professional including a medical professional type, gathering medical data from a patient, entering the medical data gathered from the patient, an urgency type for the patient, and a medical data type for the patient into a data archival system, evaluating the urgency type for the patient related to the medical data, and conducting a broadcast message to a medical professional with a medical professional type corresponding to the medical data type when the urgency type corresponds to a need for immediate reading of the medical data for the patient, and retrieving the broadcast message to the medical professional when the urgency type of the medical data changes from a first state to a second state.

The program storage device may also be configured such that the urgency type for the patient is at least one of a modality categorization, an exam priority categorization, a study data categorization and a time categorization. The program storage device wherein the method further comprises verifying the urgency type for the patient after the step of evaluating the urgency type for the patient related to the medical data and before the step of conducting the broadcast message to the medical professional.

The program storage device wherein the method further comprises reading the medical data by a medical professional. The method may further comprise changing the urgency type in the data archival system after the reading of the medical data by the medical professional.

The program storage device may also be accomplished such that the medical data type is any modality type, such as a magnetic resonance image or a computed tomography image as non-limiting examples.

The program storage device may also be accomplished such that the method further comprises creating a notification list of medical professionals of a same medical professional type; wherein the conducting of the broadcast message to the medical professional with the medical professional type corresponding to the medical data type when the urgency type corresponds to a need for immediate reading of the medical data for the patient is done through contacting medical professionals on the notification list.

An embodiment of the invention also provides an apparatus for medical data retention and medical professional notification, comprising a computer workstation configured to enter and display patient information medical data scans, a broadcast module, and a computer server connected to the computer workstation, the computer server configured to store the medical data scans patient information, the computer server also having a messaging module connected to the broadcast module, wherein the messaging module is configured to activate the broadcast module to send a message to a medical professional at a location remote from the computer workstation and the computer server based upon a predefined status of the patient information, the messaging module further configured to retrieve previously conveyed messages when a status of data corresponding to the message has changed.

DETAILED DESCRIPTION

Figure 1:
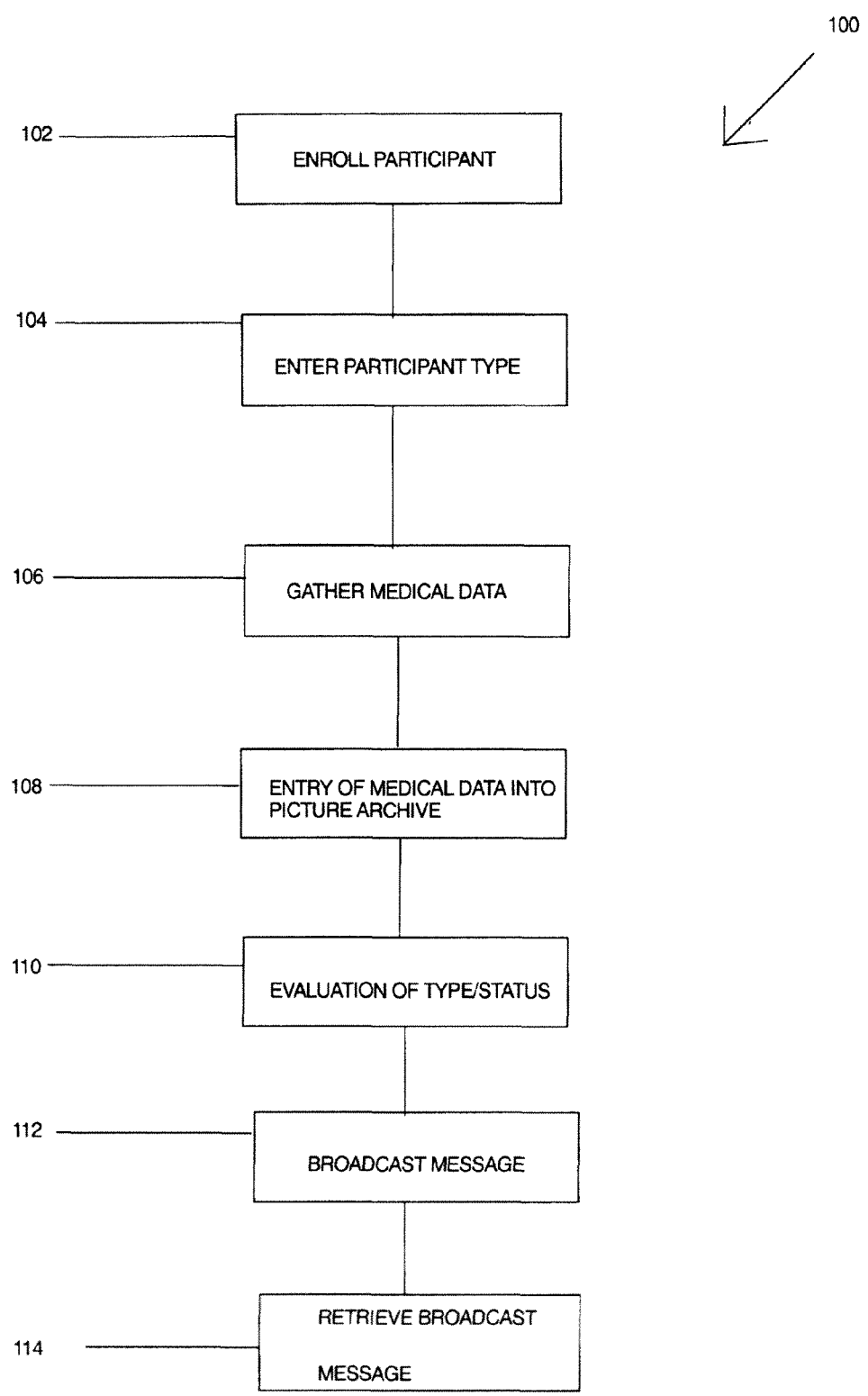
FIG. 1 is an exemplary method for picture archiving and intelligent update messaging.
Figure 2:
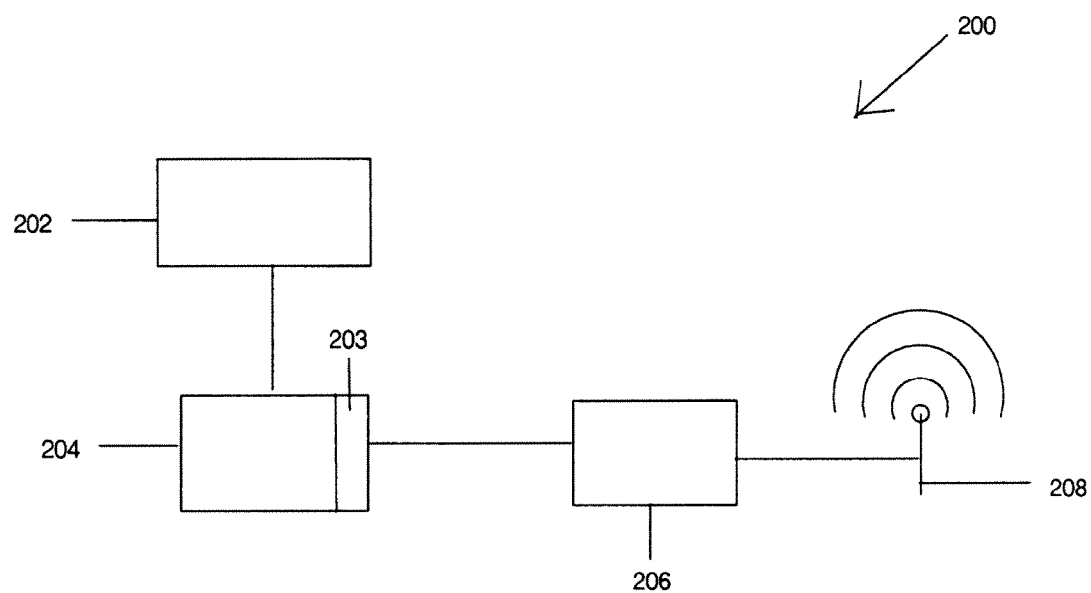
FIG. 2 is an arrangement to perform the method of picture archiving and message broadcasting.

Referring collectively to FIGS. 1 and 2, an exemplary embodiment of a method 100 for medical scan archiving and notifying medical professionals of a need for evaluation of the medical scan is presented. The different individual components used for execution of the method 100 are illustrated in FIG. 2. The method 100 for medical scan archiving and notifying medical professionals for evaluation of a medical scan with intelligent messaging update mechanism, first incorporates the step of registering/enrolling a medical professional in a system 200, the registering/enrolling of the medical professional 102 including a medical professional type 104. In an exemplary embodiment, the medical professional is a radiologist, however other types of medical professionals may also be enrolled into the system 200. As will be understood, more than one medical professional may be enrolled into the system 200 in accordance with method 100, such as dentists, who specialize in complex oral surgery and who evaluate complex data stored in data storage systems. Thus, several different types of medical professionals may be enrolled into the system 200 and the system 200 may categorize the medical professionals into discrete subgroups of areas of expertise. This can include, for example, a radiologist who specializes in reading magnetic resonance image as compared to computed tomography images. Each of the medical professionals are provided with a mobile communication device to receive messages coming from the system. As a result, the system 200 may notify individual doctors, on an as-needed basis. The communication device may be a mobile unit such as a cellular telephone with text message capability, as a non-limiting example.

Next, medical data is gathered from the patient in step 106 of the method 100. The medical data gathered from the patient may be of various types, including those specifically pertaining to visual records of patients, such as for magnetic resonance images, computed tomography scans, ultrasound and dental x-ray records as non-limiting examples. The medical data in the illustrated exemplary embodiment of the invention are scans of the patient and provided in electronic format, through a picture archiving communication system (PACS) 200.

The medical data (scans) are then stored 108 in the system 200 such as a PACS system, so that the information is archived for future use. The machinery used to obtain the scans may be directly connected to the system 200 and fed into the system memory through a data connection port or data may be fed into the system 200 through other means, such as compact disk or digital video disk.

In addition to the provision of the medical data (scans) to the computer server 204, an urgency type for the patient medical data and a medical data type for the patient are also entered. The urgency type for the patient medical data is related to the needed priority of the evaluative results. The urgency type can be configured to use a modality type, that may be, for example, any combination of an exam priority field, a required study date and time. Patient particular information may also be entered into the computer server 204, for example, patients contact information, insurance information as non-limiting examples, or may be populated by radiology information system/patient registration software. Other types of information may also be entered such that properties used to configure evaluation times, such as SQL Boolean expressions.

In one embodiment, the data stored is a magnetic resonance image that is downloaded into a computer server arrangement 204 of the system 200. The computer server 204 may be interconnected with other computer servers such that data may freely flow between computer systems. Thus, a person analyzing the medical data can be in a different location than the place that the computer data is stored, allowing medical professionals flexibility in staffing at different locations.

The method 100 then evaluates the urgency type 110 for the patient related medical data. Based upon the urgency type 110 of the patient related medical data, a broadcast message to a medical professional with a medical professional type corresponding to the medical data type when the urgency type 110 corresponds to a need for immediate reading of the medical data for the patient 112. When needed by a requesting physician (i.e. the physician requires immediate analysis of data), the system 200 allows for a broadcast to be made to ensure that attention is noted for the medical professionals conducting data evaluation. The broadcast may be made by telephone, computer email, beeper or other electronic notification to the medical professional who is performing the evaluation.

In step 114, the method 100 entails the system 200 retrieving the previously broadcasted message sent to the medical professional when the urgency type of the medical data changes from a first state to a second state.

The broadcast message may reside in the computer server 204 that is responsible for broadcasting messages to registered individuals. The messaging module 203, within the computer server 204 also examines/monitors the examination status of the data within the system 200. In an exemplary embodiment of the invention, the messaging module 203 tracks information within the system 200 such that the patient data has an examination status of "Verified," "Dictated" and "Approved" and sends out messages accordingly to medical professionals charged with reading the patient data. If the examination data satisfies a given configuration criteria, the messaging module 203 will send messages to all subscribers with the following content: patient name, study date and time, study instance UID (unique identification number), Modality, Exam Status and Procedure name. The fields of the exam information are configurable, such that a user may customize the fields/data displayed. The UID is a unique identification number that is particular to the data of the particular data set for a patient. The system 200 uses the UID in determining the status of the data set, either "Arrived," "Verified," "Dictated" or "Approved." In addition to checking the status of the examination for the status of "Verified," "Dictated" and "Approved," when the status of the examination has changed during successive time periods, then the messaging module 203 recalls/deletes previously transmitted messages onto the system 200 to ensure that the data presented to medical professionals is the most currently available.

In an exemplary embodiment of the invention, there are four exam status indicators. The four exam status indicators in the systems are 1) "Arrived"; 2) "Verified"; 3) "Dictated" and 4) "Approved." In the "Arrived" status, the images have been acquired and are present within the system 200. In the "Verified" status, an examination of the data has been verified by technologists that the correct number of images (or data) are present for reading and that the images pertain to the correct patient. In the "Dictated" status, the data has been evaluated and the results have been dictated by a staff medical professional and the report has been created. In the "Approved" status, the diagnostic report has been finalized and approved by a staff radiologist, for example.

Referring to FIG. 2 illustrating the system 200, when the medical data (image) is read by a technologist, the technologist, through the workstation 202 sends a request to the server 204 to change the data status to "Verified." In the "Verified" status, the data is ready to be evaluated. As a messaging module 203 resides in the server 204, the server 204 is able to update the broadcast module 206 to send information to broadcast module 206 and antennae 208 to the list of individuals authorized to receive such information.

When a medical data set is dictated by a medical professional, the status is then changed to "Dictated" in the server 204 through the workstation 202. The data is then ready to be read by a further medical professional, if needed, for verification. The messaging module 203 that is part of the server 204 notifies appropriately designated individuals that the medical data is in the "Dictated" status. The messaging module 203 may also identify the medical professional who dictated the data, the location of the dictation and the time and date of the dictation.

The data that has been "Dictated" may then be approved by another medical professional and the status (type) changed to "Approved." As will be understood, after the data has been changed to the "Dictated" status, the messaging module 203 within the server 204 may prepare a notification to the broadcast module 206 and antennae 208 to individuals who may be designated as performing the verification function.

An embodiment of the invention provides a method 100 and system 200 to notify radiologists that examination of medical data should commence. The invention also provides a method 100 and apparatus 200 to minimize time lag between preparation of medical data and evaluation by medical professionals so that patients receive immediate care.

The method 100 and system 200 also minimizes the need for emergency examination readings that are not necessarily needed to be processed on an expedited basis.

The method 100 and system 200 in accordance with an embodiment of the invention also discriminates between data types and subsequently allow notification of appropriate medical professionals based upon the data type required to be evaluated, as well as eliminates old information on the system to minimize down time for users.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method of notifying medical professionals of a need for evaluation of images of a medical scan, comprising the steps of:

enrolling a medical professional in a computer system, the enrolling of the medical professional including a medical professional type;

gathering medical data from a patient;

entering the medical data gathered from the patient, an urgency type for the patient, and a medical data type for the patient into a data archival system;

evaluating the urgency type for the patient related to the medical data;

conducting a broadcast message to a medical professional with a medical professional type corresponding to the medical data type when the urgency type corresponds to a need for immediate reading of the medical data for the patient;

recalling and deleting the broadcast message conducted to the medical professional in response to a determination status of a medical imaging examination has changed and the broadcast message data is not the most current that is available; and retrieving the broadcast message to the medical professional and conducting a replacement broadcast when the urgency type of the medical data changes from a first state to a second state and updating an inbox in substantially real-time with the replacement broadcast.

2. The method according to claim 1, wherein the urgency type for the patient is one of a modality categorization, an exam priority categorization, a study data categorization and a time categorization.

3. The method according to claim 1, further comprising:
verifying the urgency type for the patient after the step of evaluating the urgency type for the patient related to the medical data and before the step of conducting the broadcast message to the medical professional.

4. The method according to claim 1, further comprising:
reading the medical data by a medical professional.

5. The method according to claim 4, further comprising:
changing the urgency type in the data archival system after the reading of the medical data by the medical professional.

6. The method according to claim 1, wherein the medical data type is one of a magnetic resonance image and a computed tomography image.

7. The method according to claim 1, wherein the medical data type is a modality type contained in a picture archiving and communication system.

8. The method according to claim 1, further comprising:
creating a notification list of medical professionals of a same medical professional type, wherein the conducting of the broadcast message to the medical professional with the medical professional type corresponding to the medical data type when the urgency type corresponds to a need for immediate reading of the medical data for the patient is done through contacting medical professionals on the notification list.

9. A non-transitory program storage device readable by machine, tangibly embodying a program of instructions executable by the machine to perform method steps for medical scan archiving and notifying medical professionals of a need for evaluation of images of a medical scan, comprising the steps of:
enrolling a medical professional in a computer system, the enrolling of the medical professional including a medical professional type; gathering medical data from a patient;
entering the medical data gathered from the patient, all urgency type for the patient, and a medical data type for the patient into a data archival system;
evaluating the urgency type for the patient related to the medical data; and conducting a broadcast message to a medical professional with a medical professional type corresponding to the medical data type when the urgency type corresponds to a need for immediate reading of the medical data for the patient;
deleting the broadcast message conducted to the medical professional from an inbox of the medical professional in response to a determination status of a medical imaging examination has changed and the broadcast message data is not the most current that is available; and
retrieving the broadcast message to the medical professional when the urgency type of the medical data changes from a first state to a second state and updating an inbox in substantially real-time with the replacement broadcast.

10. The program storage device according to claim 9, wherein the urgency type for the patient is one of a modality categorization, an exam priority categorization, a study data categorization and a time categorization and including
recalling the broadcast message conducted to the medical professional in response to a determination status of a medical imaging examination has changed and the broadcast message data is not the most current that is available.

11. The program storage device according to claim 9, wherein the method further comprises:
verifying the urgency type for the patient after the step of evaluating the urgency type for the patient related to the medical data and before the step of conducting the broadcast message to the medical professional.

12. The program storage device according to claim 9, wherein the method further comprises reading the medical data by a medical professional.

13. The program storage device according to claim 12, wherein the method further comprises:
changing the urgency type in the data archival system after the reading of the medical data by the medical professional.

14. The program storage device according to claim 9, wherein the medical data type is a magnetic resonance image.

15. The program storage device according to claim 9, wherein the medical data type is a computed tomography image.

16. The program storage device according to claim 9, wherein the method further comprises:
creating a notification list of medical professionals of a same medical professional type; wherein the conducting of the broadcast message to the medical professional with the medical professional type corresponding to the medical data type when the urgency type corresponds to a need for immediate reading of the medical data for the patient is done through contacting medical professionals on the notification list.

17. An apparatus for medical data retention and medical professional notification, comprising:
a computer workstation configured to enter and display patient information medical data scans;
a broadcast module; and
a computer server connected to the computer workstation, the computer server configured to store the medical data scans patient information, the computer server also having a messaging module connected to the broadcast module, wherein the messaging module is configured to activate the broadcast module to send a message to a medical professional at a location remote from the computer workstation and the computer server based upon a predefined status of the patient information, the messaging module is further configured to retrieve previously conveyed messages when a status of data corresponding to the message has changed and to at least one of, (a) delete and (b) recall, from an inbox, previously conveyed messages in response to a determination status of a medical imaging examination has changed and the broadcast message data is not the most current that is available and updating an inbox in substantially real-time.

* * * * *